(12) United States Patent
Saishin et al.

(10) Patent No.: US 6,413,262 B2
(45) Date of Patent: Jul. 2, 2002

(54) METHOD OF CRYSTALLINE LENS REPLACEMENT

(75) Inventors: Motosugu Saishin, Osaka (JP); Mitsuo Tsukamoto, 1-14-5, Ohiraki, Fukushima-ku, Osaka-shi, Osaka 553-0007 (JP); Aizo Yamauchi, 2-14-10, Midorigaoka, Atsugi-shi, Kanagawa 243-0041 (JP)

(73) Assignees: Mototsugu Saishin; Mitsuo Tsukamoto; Aizo Yamauchi; Yoshiaki Hara, all of (JP)

( * ) Notice: Subject to any disclaimer, the term of this patent is extended or adjusted under 35 U.S.C. 154(b) by 0 days.

(21) Appl. No.: 09/805,966

(22) Filed: Mar. 14, 2001

(30) Foreign Application Priority Data

Mar. 14, 2000 (JP) .......................................... 2000-070189

(51) Int. Cl.$^7$ .............................. A61B 17/00; A61F 2/14
(52) U.S. Cl. ........................................ 606/107; 623/6.56
(58) Field of Search .......................... 606/1, 107, 166, 606/170; 623/4.1, 6.56, 6.61

(56) References Cited

U.S. PATENT DOCUMENTS

| 4,681,102 | A | * | 7/1987 | Bartell |
| 4,709,996 | A | * | 12/1987 | Michelson |
| 4,731,079 | A | * | 3/1988 | Stoy |
| 5,476,515 | A | * | 12/1995 | Kelman et al. |

FOREIGN PATENT DOCUMENTS

| JP | 1-227753 | 9/1989 |
| JP | 2-255151 | 10/1990 |

OTHER PUBLICATIONS

Kessler, Julius, M.D., Experiments in Refilling the Lens, Mar. 1964, Archives of Ophthalmology.
Kessler, Julius, M.D., Refilling the Rabbit Lens, Oct. 1966, Archives of Ophthalmology.
Kessler, Julius, M.D., Lens Refilling and Regrowth of Lens Substance in the Rabbit Eye, Aug. 1975, Annals of Ophthalmology.
Agarwal, Lalit P., Narsimhan, E. C., and Mohan, Madan, Experimental Lens Refilling, 1967, Orient. Arch. Ophthal.
Parel, J. M., Gelender, H., Trefers, W. F., Norton, E. W. D., Phaco–Ersatz: cataract surgery designed to preserve accommodation, 1986, Graefe's Archive for Clinical and Experimental Ophthalmology.

* cited by examiner

Primary Examiner—Henry J. Recla
Assistant Examiner—William W. Lewis
(74) Attorney, Agent, or Firm—Marshall, Gerstein & Borun

(57) ABSTRACT

A method of crystalline lens replacement for eyes comprises the steps of forming a small hole that penetrates through the lens capsule, removing a part of the crystalline lens substance through the hole, refilling the lens capsule by injecting a composition comprising a hydrophilic polymer directly into the lens capsule, and closing the hole. The method of crystalline lens replacement may be performed on animals or humans. Furthermore, the method of crystalline lens replacement may be performed on a patient suffering from cataract, where the opaque crystalline lens substance in the lens capsule is removed.

21 Claims, 6 Drawing Sheets

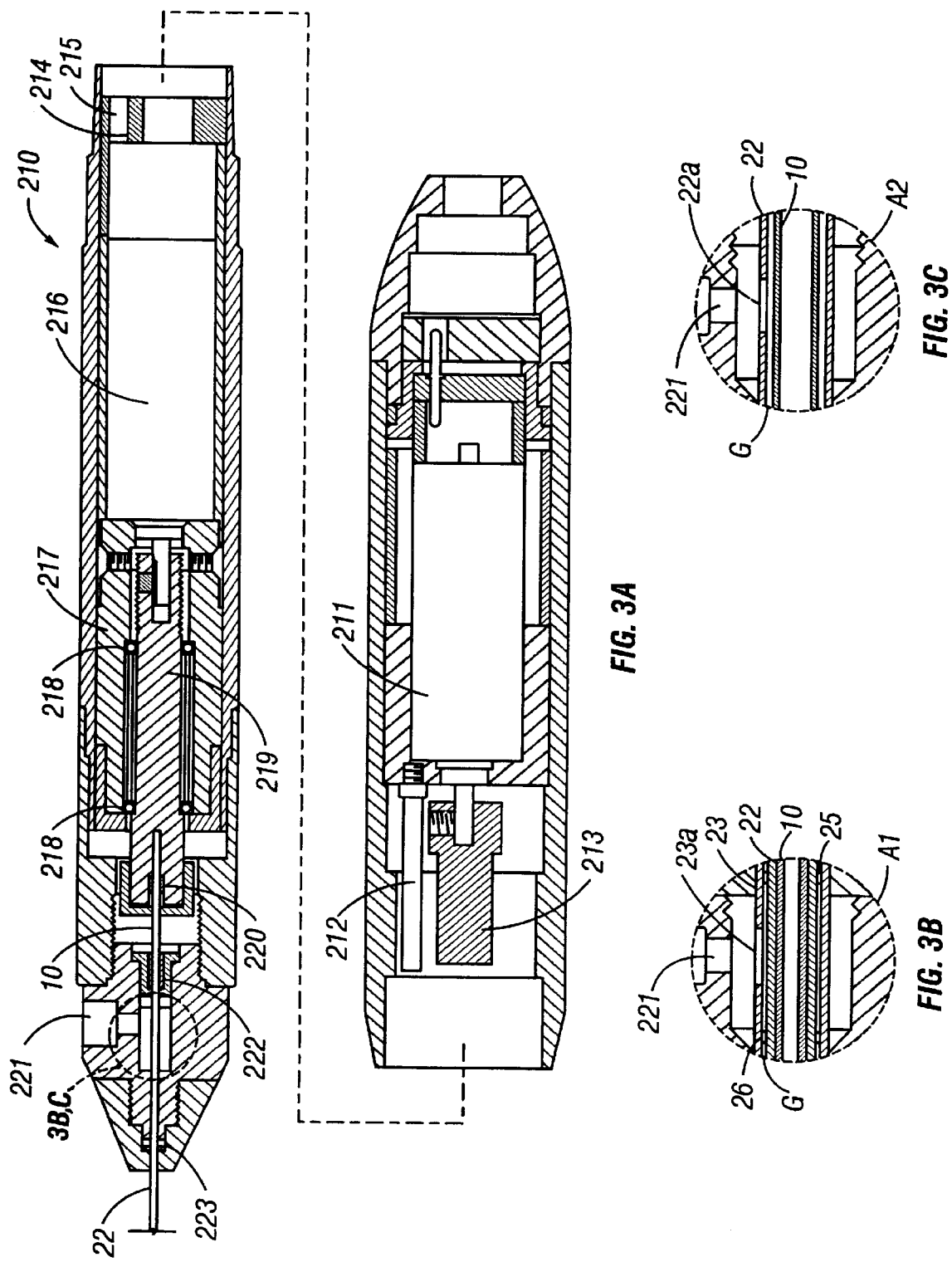

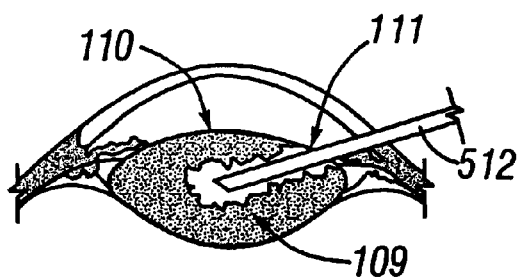
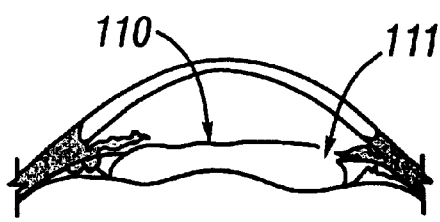
FIG. 8A  FIG. 8B
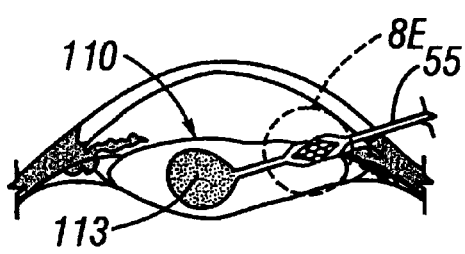
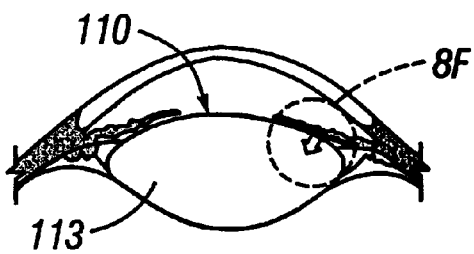
FIG. 8C  FIG. 8D
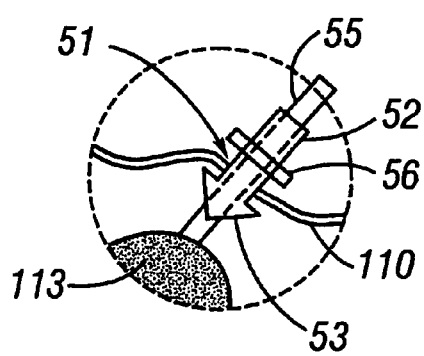
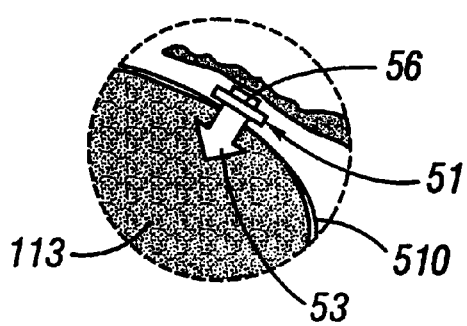
FIG. 8E  FIG. 8F

METHOD OF CRYSTALLINE LENS REPLACEMENT

FIELD OF THE INVENTION

The present invention relates to a method of crystalline lens replacement. More particularly, the present invention relates to a method of crystalline lens replacement for restoring optical properties, such as clarity and refraction, of the lens suffering from defects (e.g., cloudiness, complete opacification or loss of transparency) due to cataracts or other diseases, while keeping the ability of the normal lens to accommodate resulting from the relaxation and contraction of the ciliary muscle.

DESCRIPTION OF THE PRIOR ART

Cataract is a disease involving partial or complete opacity in/on the lens or capsule of the eye(s), which could result in significant loss of eyesight or even blindness. Cataracts can be classified to congenital or acquired, and known acquired cataracts include senile (age-related), diabetic and traumatic cataracts as well as other types thereof that may develop upon exposure to energy such as ultraviolet or nuclear radiation. Among these, senile cataracts are one of the most commonly found disorders of the middle aged and elderly persons, of which patients have increased through recent improvements in living conditions, nutrition, and medical infrastructures resulting in an increase in life expectancy.

Several procedures are used in the therapeutic treatment of cataracts. One technique is called extracapsular lens extraction that involves surgical removal of the cloudy lens cells, leaving the outer membrane lens capsule intact. Once the content of the lens is removed, cataract glasses, contact lenses or intraocular lenses may be utilized for replacement so that the post-extraction corrective eyesight is provided. The term "intraocular lens" as used herein means a plastic lens having an optic (lens body) and haptics (fixation elements), in which the optic is made of a molded polymer or a hydrated polymer gel and each haptic comes out of the optic to adjoin the lens to the iris or capsule. Intraocular lenses (IOLs) are artificial lenses that have been rapidly widespread because they can provide with better eyesight than glasses or contact lenses after surgery, the posterior capsule can be left in its place by virtue of the established procedures such as ultrasonic phacoemulsification, and good post-surgical results have afforded at a lower rate of complications. The intraocular lenses may be made of a hard plastic material such as polymethylmethacrylate (PMMA), or of either a soft hydrated polymer such as poly(2-hydroxyethylmethacrylate) and poly(N-vinyl-2-pyrrolidone) or a soft non-hydrated material such as silicon rubber and acrylic rubber.

The crystalline lens of the normal eyes usually accommodate by changing their shapes to allow the eyes to adjust their focal point. On the other hand, the above-mentioned plastic intraocular lenses having a predetermined shape are disadvantageous owing to their inabilities of adjusting their focal point. In this respect, intraocular lenses with multifocal optics are also employed to adjust for both short- and long-range eyesight. However, such multifocal IOLs rely on the pupil that serves as the aperture stop in an optical system, so that they provide with double images, namely simultaneously distant and near images, which may result in unpleasant visual experiences. In particular, the elderly persons can hardly accommodate themselves to such new experiences in eyesight, therefore clinical applications of the multifocal IOLs have been significantly limited. In addition, the above-described surgical procedure also has a problem involved in a relatively large hole required for removal of the lens substance and placement of the intraocular lens.

Taking into account of such circumstances, implantation of a soft artificial lens that can change its form has been attempted to provide accomodation of a natural lens. For example, J. Kessler reported that refilling of the lens capsule with clear injectable silicone compounds in animal eyes can restore the shape of a normal lens (Kessler J. Experiments in refilling the lens, Arch. Ophthalmol. 71 [3]:412–417 (1964)). However, time-dependent leakage of the injected liquid silicone deforms the lens in a relatively short period of time, thus resulted in difficulty in keeping appropriate eyesight of the patient. Accordingly, such a refilling procedure cannot be applied in practice to an in vivo treatment of cataracts.

Some other conventional procedures have been developed to overcome the above-mentioned problems, for example: (1) a method comprising injection of an intraocular lens composition containing a photo-polymerizable monomer and a photoinitiator directly into a lens capsule after removal of the lens substance, or into an intracapsular balloon or a capsule of a thin film that was inserted into the lens capsule (Japanese Patent Laid-open No. 2-255151); and (2) a method comprising replacement of the natural lens with a balloon or a capsule of a thin film into which a polymer solution or a cross-linking gel is injected after removal of the lens substance (Japanese Patent Laid-open No. 1-227753).

The above first approach is disadvantageous in: that no accommodation can be achieved due to the formation of a solid intraocular lens in the lens capsule; that only insufficient eyesight can be provided because of difficulties in forming an intraocular lens of an exactly desirable shape; that the monomer and/or photoinitiator may affect harmfully in in vivo upon absorption into the body of organisms; and that sterilization of the composition is rather difficult.

The above second approach of injecting the liquid polymer into the balloon is disadvantageous in that it is difficult to conform the balloon to the shape of the lens capsule even when an elastomer is used as the material of the balloon, and that only insufficient and unstable visual performance can be obtained. Furthermore, since a fairly large incision in the sclera, cornea, and/or lens capsule is required, the procedure is much invasive for the patient.

SUMMARY OF THE INVENTION

Accordingly, an object of the present invention is to provide a method of ophthalmic treatment of diseases such as cataracts with a good prognosis by means of replacing the lens suffering from defects (e.g., cloudiness, complete opacification or loss of transparency) due to cataracts or other diseases, while keeping the functions (e.g., accommodative ability) and the fundamental structure of the normal lens to restore optical properties, such as clarity and refraction, with minimal invasive operation to the lens and its circumferential tissues.

The present inventors have established the following method comprising the steps of:

(1) forming a small hole penetrating through a crystalline lens capsule for removing crystalline lens cells that are clouded and opacified, and for refilling an injectable composition directly into the lens capsule thereafter, so that the hole may be as small as possible with a smooth periphery;

(2) removing the opacified crystalline lens substance without damaging the hole;

(3) refilling directly into the lens capsule an injectable composition that is safe for an organism, capable of being readily injected without any damage to the hole, to yield suitable refractive power; and (4) firmly closing the hole after the injectable composition is directly refilled into the lens capsule.

A first aspect of the present invention is to provide a method of crystalline lens replacement, comprising the steps of:

(1) forming a small hole penetrating through a crystalline lens capsule;

(2) removing at least a part of the crystalline lens substance through the hole;

(3) refilling the crystalline lens capsule with an injectable composition to be refilled directly into the lens capsule comprising a hydrophilic polymer through the hole; and (4) closing the hole.

In this first aspect of the present invention, it is preferable that the hole may be closed by using a hole closure comprising a rod-shaped member made of a gel or a soft plastic material having an enlarged portion provided at the tip of the rod-shaped member, a marginal protruding piece provided at a middle part of the rod-shaped member, and a closed tubular section provided along the axial center of the rod-shaped member.

In the preferred embodiment, the hole closure may have the closed tubular section penetrating from a tip of the enlarged portion to a tail end of the rod-shaped member, alternatively, the closed tubular section may be formed such that it extends from inside the enlarged portion to the tail end of the rod-shaped member while enabling to pass through the length from the anterior edge of the closed tubular section to the tip of the enlarged portion.

Moreover, it is preferable that the hole closure includes a rigid tubular member that is longitudinally slidable in the closed tubular section and removable therefrom.

Furthermore, it is preferable that the step (4) described above may be carried out by: inserting the rigid tubular member in the closed tubular section of the hole closure; inserting the enlarged portion provided on the tip of the closure into the crystalline lens through the hole; pinching a portion of the lens capsule surrounding the hole with a rear edge surface of the enlarged portion and an anterior edge surface of the marginal protruding piece; and then pulling out the rigid tubular member, thereby closing the hole with the remaining closure.

A second aspect of the present invention is to provide to a method of crystalline lens replacement, comprising the steps of:

(1) forming a small hole penetrating through a crystalline lens capsule;

(2) inserting a rigid tubular member that is longitudinally slidable in and removable from a closed tubular section, into the closed tubular section of a hole closure comprising a rod-shaped member made of a gel or a soft plastic material having an enlarged portion provided at the tip of the rod-shaped member, a marginal protruding piece provided at a middle part of the rod-shaped member and the closed tubular section provided along the axial center of the rod-shaped member, thereafter inserting said enlarged portion through the hole into the crystalline lens;

(3) ejecting a head of the rigid tubular member from the tip of the enlarged portion, and removing the crystalline lens substance through the rigid tubular member;

(4) refilling the crystalline lens capsule with an injectable composition to be refilled directly into the lens capsule comprising a hydrophilic polymer through the rigid tubular member; and (5) pinching a portion of the lens capsule surrounding the hole with a rear edge surface of the enlarged portion and an anterior edge surface of the marginal protruding piece, and then pulling out the rigid tubular member thereby closing the hole with the remaining closure.

Preferably, the hole closure for use in the first and second aspects of the present invention may have a separate removable ring member as the marginal protruding piece, and the rigid tubular member that is longitudinally slidable in and removable from the closed tubular section. In addition, the gel may preferably comprise cross-linked polyvinyl alcohol, and the soft plastic may be preferably silicon rubber.

In the present invention described heretofore, it is preferable that 1 to 90% by weight of hydrophilic polymer may be contained in the injectable composition to be refilled directly into the lens capsule.

Furthermore, it is preferable that the injectable composition to be refilled directly into the lens capsule may have a viscosity of 50,000 cP or lower, an index of refraction of 1.340 or higher and a visible light transmittance of 50% or more. Moreover, in the preferred embodiment of the invention, the hydrophilic polymer may be at least one polymer selected from the group consisting of polyvinyl alcohol polymers, polyvinyl pyrrolidone polymers and polyethylene glycol polymers, and more preferably, the hydrophilic polymer may comprise a polyvinyl alcohol polymer and a polyvinyl pyrrolidone polymer. When such an injectable composition is directly refilled into the lens capsule followed by closing, a shape can be achieved substantially corresponding to the natural shape of the crystalline lens before removing the lens substance, and thus, an accommodative ability can be imparted to the lens implant on the basis of the changes in the shape of the crystalline lens resulting from the relaxation and contraction of the ciliary muscle, as is originally found in a natural crystalline lens.

In the preferred embodiment of the above-mentioned present invention, the subject of the method of replacement may be animals including human, particularly a patient suffering from cataract, wherein the opacified crystalline lens substance may be removed at the step (2).

In yet further embodiment of the present invention, the hole may be preferably formed by irradiation of laser beam, or by using a cystotome hand piece at the step (1). In the case in which the hole is formed by irradiation of the laser beam, a light guide may be preferably used which comprises a condensing lens having a focal length of 1 to 500 mm provided on a tip of the guide. Meanwhile, it is preferable that the cystotome hand piece may comprise a rotary shaft, a first motor for rotating the rotary shaft, a second motor for longitudinally moving the first motor and the rotary shaft integrally, a trepan bar removably attached to a tip of the rotary shaft, a fixed outer casing through which the trepan bar is inserted, and negative pressure application means for applying a negative pressure to an interspace of an inside of the trepan bar and/or between the trepan bar and the fixed outer casing, wherein the rotary shaft provided integrally with the first motor is moved forward through the second motor to eject a tip of the trepan bar from the outer casing during the hole forming operation, and the rotary shaft provided integrally with the first motor is usually moved backward through the second motor to store the tip of the trepan bar within the outer casing.

A preferred embodiment of the present invention is described below in more detail.

BRIEF DESCRIPTION OF THE DRAWINGS

FIG. 3 is a view showing the structure of a main part of the cystotome hand piece according to yet another embodiment of the present invention.

DESCRIPTION OF THE PREFERRED EMBODIMENT (1) Formation of a Hole Penetrating through a Crystalline Lens Capsule In a method of crystalline lens replacement according to the present invention, a step of forming a hole penetrating through a crystalline lens capsule is carried out first. In order to facilitate the following steps of removal of the crystalline lens substance and the refilling of a injectable composition directly into the lens capsule, and to minimize invasion as little as possible, the hole may have a diameter of 7 mm or less, preferably 2 mm or less, more preferably 1 mm or less and further preferably 0.1 mm or less. In addition, the injectable composition should be prevented from leaking out of the closed region for a long period of time, after the injectable composition is directly refilled into the lens capsule and the hole is closed. Therefore, it is desirable that an almost completely cylindrical hole is formed having a smooth edge without any uneaven or sawtooth-like portion.

Thus, according to the present invention, it is preferable that formation of a small hole may be carried out by irradiation of laser beam, or by using a cystotome hand piece so that a hole having a desirable size and shape can be formed.

Figure 1:
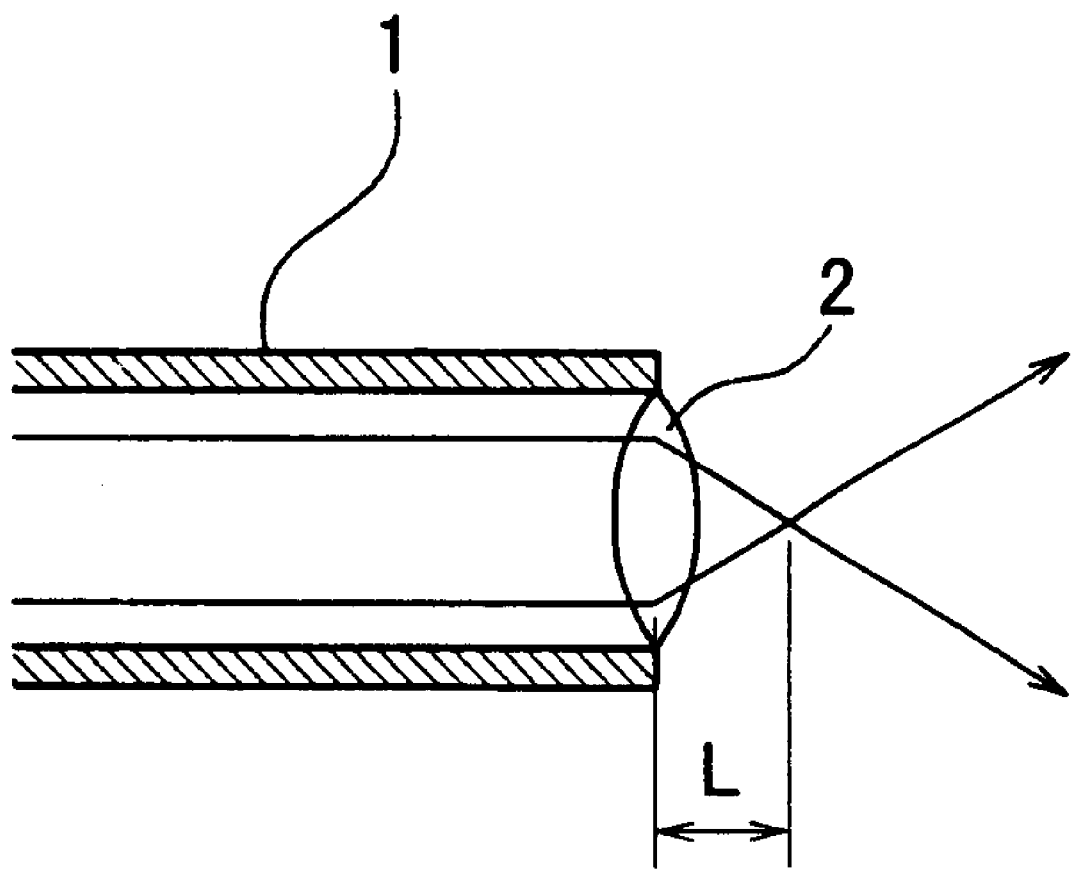
FIG. 1 is a sectional view schematically illustrating a part of a light guide for laser beam irradiation for forming a hole according to one embodiment of the present invention.

In the case in which the formation of a hole is carried out by irradiation of the laser beam, a light guide 1 (see, FIG. 1 showing a partial schematic view) may be preferably used which comprises a condensing lens 2 provided on a tip of the guide. Inside the light guide 1, a fiber bundle is included comprising a large number of fibers. The fiber bundle usually has a diameter predetermined to be approximate to the diameter of a hole to be formed thereby. More specifically, according to the present invention, a light guide 1 used for irradiation of the laser beam may comprise a fiber bundle having a diameter of 7 mm or less, preferably 2 mm or less, more preferably 1 mm or less and particularly preferably 0.1 mm or less.

In order to reduce the irradiation amount of energy per unit area as much as possible which may pass through the crystalline lens to reach and damage various tissues positioned therebehind, for example, a vitreous body, a retina, a choroid, a ciliary corpusciliary corpus, an optic nerve, a blood vessel and the like, a focal length L of the condensing lens 2 may be preferably determined to be ranging from 1 to 2000 mm, more preferably 1 to 50 mm such that the beam can be scattered at a wide angle following condensation. When the focal length L is too long, comparatively condensed beam may be emitted following trepanation of the crystalline lens, accordingly, too high irradiation amount of energy per unit area on the tissues behind the crystalline lens may be resulted so that these tissues may be damaged. Such a focal length can be determined by properly selecting a radius of curvature of the condensing lens 2 and an index of refraction of a lens material. Suitably, a lens having a high index of refraction, or a gradient refraction index lens can be used.

Additionally, the small hole can be formed successfully without using the condensing lens by properly selecting the kind or output power of a laser beam source and the design of the light guide, or by using another condensing device, alternatively, by using means for selectively condensing laser energy onto the crystalline lens capsule, for example, by applying a pigment solution of which color is complementary to the beam (such as indocyanine green for red light) capable of increasing an absorption ability.

Various kinds of conventional laser beam sources may be used, accordingly, a solid-state laser, a liquid laser, a gas laser and a semiconductor laser or the like can be employed. Desirably, a laser capable of providing such a wavelength and intensity as being advantageous in controlling the diameter of the hole and the intensity at the margin of a hole may be employed, for example, an erbium laser, an Nd: YAG laser, an excimer laser or a carbon dioxide laser.

The wavelength of the laser beam may range from ultraviolet, visible to near infrared, in particular, may be 200 to 1500 nm, more preferably 400 to 800 nm in terms of possibilities to minimize an error upon the use of aiming light.

Although it is important that an almost completely cylindrical hole can be formed having a smooth edge as described above, the output power of the laser beam should be regulated so that the amount of laser exposure to the tissues behind the crystalline lens is controlled to be a value which is lower than a maximum permissible exposure (MPE) of the International Electrotechnical Commission (IEC) (Laser Application Technology Handbook, Laser Association ed., (Apr. 1, 1989, first edition No. 4, Asakura Shoten), Chapter VIII, see Table 8.2).

It is preferable that a distance between a crystalline lens capsule surface and a tip of a light guide be reduced as much as possible in order to control the diameter of the hole while condensing the thermal energy at the maximum extent onto the surface to form a hole and minimizing damage on circumferential tissues.

Furthermore, by using a processing means capable of scanning to provide an intensive action of processing energy on the surface of the crystalline lens capsule to form a hole instead of using a laser beam. For example, by way of a high frequency electric current stimulation, a hole can be formed so that the tissues behind the crystalline lens may be prevented from damage through scattering of the energy in such an area behind the crystalline lens, without adverse effects on the circumferential tissues are not affected.

Figure 2A:
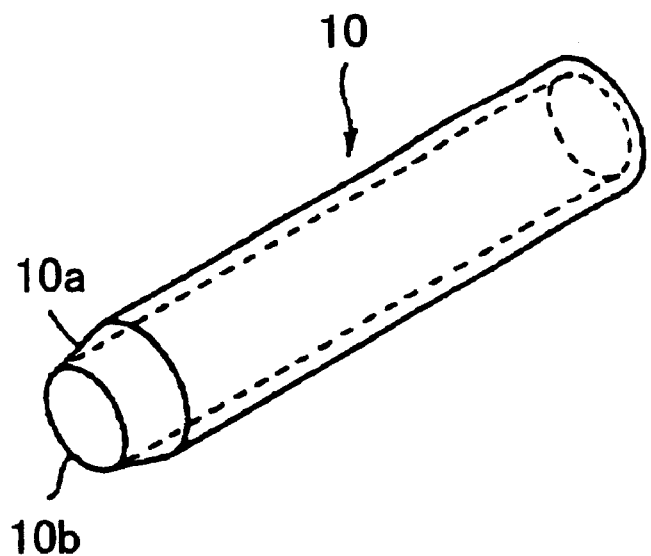
FIGS. 2(A) and 2(B) are perspective and sectional views showing an example of a trepan bar for use in a cystotome hand piece and an example of how it may be used according to another embodiment of the present invention, respectively.

As described in Japanese Laid-Open Patent Publications Nos. 10-212 (1998) and 10-328225 (1998) and the like, for example, a cystotome hand piece to be another candidate as means for forming a hole usually comprises a trepan bar 10 which is a cylindrical (tubular) cutter having a taper portion 10a provided in a tip end thereof with a tip 10b being a blade as shown in FIG. 2A.

The Japanese Laid-Open Patent Publication No. 10-212 discloses a hand piece in which a trepan bar is movably provided back and forth within a head portion. Upon forming a hole through pushing the blade provided on the tip of the trepan bar against an outer membrane 110 of a crystalline lens capsule while rotating the blade, a suction tube is connected to an outer casing 11 or the trepan bar, thus a negative pressure is applied within the head outer casing or the trepan bar 10 using a vacuum device operated before or during the trepanation, thereby sucking the outer membrane 110 of the crystalline lens capsule into the tip of the trepan bar 10 while the rotation of the trepan bar 10 is carried out (see FIG. 2B).

Moreover, the Japanese Laid-Open Patent Publication No. 10-328225 (1998) has discloses a hand piece comprising a movable rotary shaft which is axially movable and is connected to a trepan bar directly or through a relay rotary shaft such that a trepanation work is started after the rotating speed of the trepan bar is fully increased, a rotary shaft which is rotated by a power source such as a motor and serves to connect the movable rotary shaft to be movable axially, an outer casing having the trepan bar as an inner casing, and an actuator (operation pole) for axially moving the movable rotary shaft, which are not shown in Figures, wherein the tip of the trepan bar is moved backward into the outer casing, the power source is driven and the actuator is then driven after a predetermined time passes, and the tip of the trepan bar is ejected from the tip of the outer casing by a predetermined amount so that the trepanation work can be perfected. According to this type of hand piece, the length of ejection of the trepan bar from the outer casing can be controlled to be a predetermined length (for example, approximately 3 mm because the crystalline lens has a thickness of approximately 4 mm). Consequently, the trepan bar does not enter the crystalline lens at en excess length so that safety can be expected. In addition, air is sucked through the trepan bar and the outer casing during the trepanation work, therefore, the outer membrane surface of the crystalline lens is sucked toward the blade portion of the trepan bar, thus coherent contact with the blade portion is resulted. Consequently, a smooth hole can be obtained.

More preferably, a hand piece 210 may be used which comprises a rotary shaft 219, a first motor 216 for rotating the rotary shaft 219 (a motor for rotating a trepan bar), a second motor 211 for longitudinally moving the first motor 216 and the rotary shaft 219 integrally (a motor for moving trepan bar), a trepan bar 10 to be removably attached to a tip of the rotary shaft 219, a fixed outer casing 22 through which the trepan bar 10 is to be inserted, and negative pressure application means for applying a negative pressure into the trepan bar 10 and/or a space between the trepan bar 10 and the fixed outer casing 22 as shown in FIG. 3, the rotary shaft 219 integral with the first motor 216 being moved forward through the second motor 211 to eject the tip of the trepan bar 10 from the outer casing 22 during a trepanation work, and the rotary shaft 219 integral with the first motor 216 being usually moved backward through the second motor 211 to put the tip of the trepan bar 10 in the outer casing 23.

Embodiments of the trepan bar 10 to be applied to the cystotome hand piece 210 are detailed, which can be suitably utilized at the step of forming a hole according to the present invention as described above.

Figure 2B:
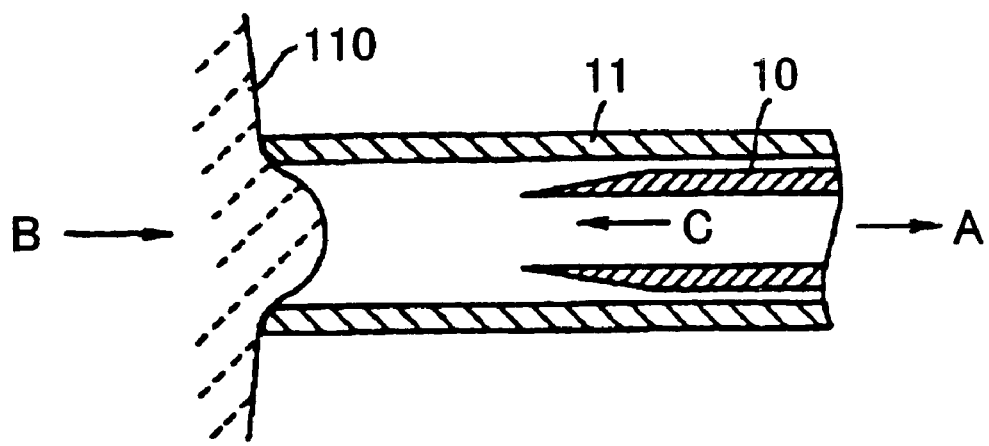

In an embodiment shown in FIG. 2B, a tip of the outer casing 11 is brought to contact with the crystalline lens capsule outer membrane 110 and air is sucked away to the trepan bar 10 and/or through a space between the trepan bar 10 and the outer casing 11 (that is, the inside of the outer casing 11) in a direction of an arrow A. Consequently, the outer membrane 110 is sucked in a direction of an arrow B to be protruded thereby applying a tension to the surface of the outer membrane 110. Then, the trepan bar 10 is rotated and moved forward in a direction of an arrow C, thereby cutting the outer membrane 110 to form a hole.

Figure 4A:
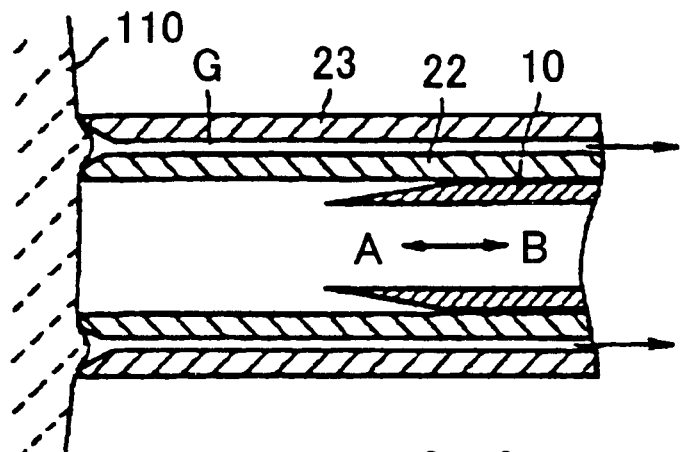
FIGS. 4(A), 4(B) and 4(C) are sectional views showing an example in which a trepan bar is used in a cystotome hand piece according to a further embodiment of the present invention.
Figure 4B:
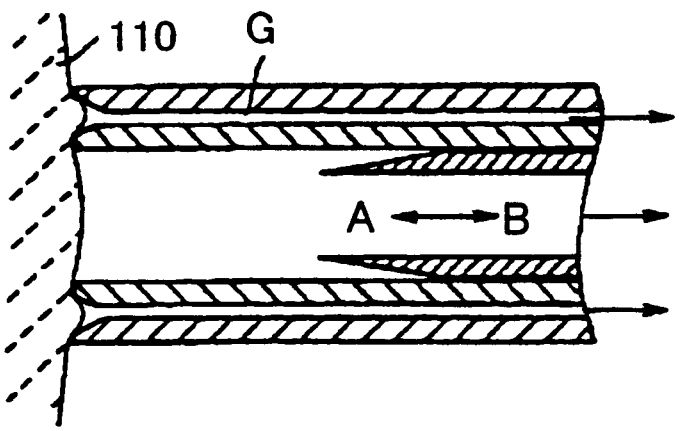
Figure 4C:
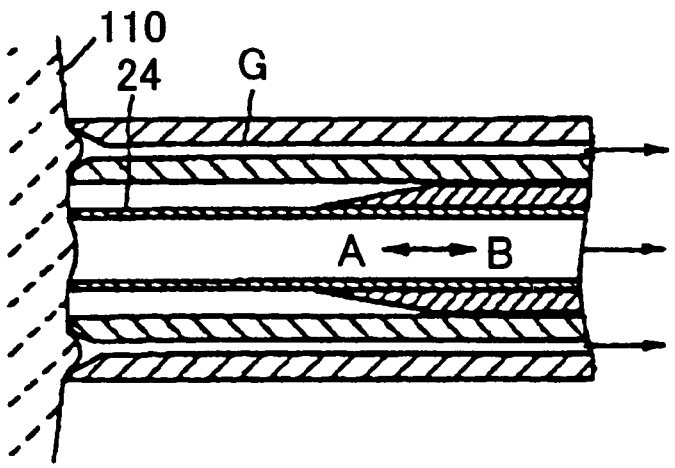

In FIGS. 4A to 4C, the reference numeral 10 also denotes a trepan bar, while the reference numeral 22 denotes an outer casing; and the reference numeral 23 denotes an outer casing provided coaxially on the outside of the outer casing 22 with a predetermined space G with respect to the outer casing 22. The outer casings 22 and 23 constitute a double tube. As shown in FIG. 4C, the reference numeral 24 denotes an inner casing (center pipe) provided within the trepan bar 10. The trepan bar 10 can be moved in the directions of arrows both of A and B, and the outer casings 22 and 23 and the inner casing 24 are fixed.

In the embodiment shown in FIG. 4A, suction is carried out through the space G between the outer casings 22 and 23. Thus, the outer membrane 110 is sucked through the space G portion and is pulled out flatly on the front surface of the outer casing 22, and the tip portion (blade portion) of the trepan bar 10 contacts on the outer membrane 110 thus pulled out flatly, that is, the blade tip of the trepan bar 10 simultaneously contacts on such a flat surface. Consequently, the trepanation can be reliably carried out to yield a hole having a more preferable shape.

In the embodiment shown in FIG. 4B, in addition to the example shown in FIG. 4A, the suction is further carried out through the inside of the trepan bar 10. Consequently, the outer membrane 10 in the tip portion of the trepan bar 10 is pulled out toward the front surface of the outer casing 22 by greater force than that in the case shown in FIG. 4A (although the outer membrane 110 is slightly protruded into the outer casing 22) so that the surface of the outer membrane 110 becomes smoother. Accordingly, the trepanation can be carried out to yield a hole having a more preferable shape.

In the embodiment shown in FIG. 4C, the inner casing 24 is provided in the trepan bar 10, and the suction is carried out within the inner casing 24 through the space G between the outer casings 22 and 23. Thus, the outer membrane 110 is flatly pulled out between the outer casing 22 and the inner casing 24 as shown, and the blade tip of the trepan bar 10 contacts on the portion thus pulled out flatly. Therefore, the trepanation can be more reliably carried out to give a more preferable shape to the outer membrane 110.

FIG. 3 is a sectional view illustrating the structures of the main parts of a hand piece ($A_1$) comprising the trepan bar 10 and the outer casings 22 and 23 having the structure shown in FIG. 4A and a hand piece ($A_2$) comprising the trepan bar 10 and the outer casing 22 having the structure shown in FIG. 4B. The reference numeral 210 denotes the hand piece (a vacuum hose and a power cord are not shown). The trepan bar moving motor 211 for moving the trepan bar 10 forward or backward as well as the trepan bar rotating motor 216 for rotating the trepan bar 10 are provided within the hand piece 210, and a portion between the outer casings 22 and 23 is sucked to bring the outer membrane to close contact with the tips of the outer casings 22 and 23. In such a state, the trepan bar 10 is moved forward, and rotated through the motors 211 and 216. Thus, the trepanation of the lens capsular outer membrane 110 is achieved.

Next, a mechanism for moving the trepan bar 10 forward or backward through the motor 211, while rotating the trepan bar 10 through the motor 216 is detailed. The rotating movement of the motor 211 is transmitted to a bolt 213 (feed screw) connected to the rotary shaft of the motor 211. The bolt 213 is screwed into a nut 214 mounted to the motor 216. Moreover, a bar 212 for stopping rotation is protruded from the motor 211, and a tip portion of the bar 212 is engaged with a concave portion 215 provided on the motor 216 side. Accordingly, when the motor 211 is rotated leading to rotation of the bolt 213, the nut 214 mounted to the motor 216 is moved forward or backward, depending on the direction of the rotation of the motor 211. On the other hand, the rotating movement of the motor 216 is transmitted through a bearing 218 to the rotary shaft 219 rotatably supported on a movable member 217 constituted integrally with the motor 216, and an end of the trepan bar 10 is inserted and fixed into an O ring 220 provided in the tip portion of the rotary shaft 219.

Accordingly, when the motor 211 is rotated, the motor 216 and the rotary shaft 219 are moved forward or backward together with the movable member 217 in the direction of the rotation of the motor 211. Consequently, the trepan bar 10 is also moved forward or backward and the motor 216 is rotated so that the trepan bar 10 is rotated. Thus, the trepan bar 10 is rotated and moved forward so that trepanation of the outer membrane of the crystalline lens capsule can be accomplished.

The trepan bar 10 is rotatably inserted into the outer casing 22 as shown in FIG. 4A, and the space G is provided between the outer casings 22 and 23. A negative pressure is applied to the outer membrane 110 through the space G. In FIG. 3, a portion A shows a mechanism for applying a negative pressure to the space G. In more detail, the structure of the portion A is enlarged as a portion $A_1$ in FIG. 3.

In FIG. 3, the reference numeral 221 denotes a vacuum application port for applying a negative pressure to the space G between the outer casings 22 and 23. A vacuum tube that is connected to a vacuum device (not shown) is connected to the vacuum application port 221. The negative pressure derived from the vacuum application port 221 is transferred to the space G between the outer casings 23 and 22 through an opening 23a provided on the outer casing 23. The space G between the outer casings 23 and 22 is provided and kept by a sealing ring 25 behind the opening 221 (the rotary shaft 219 side) and a ring 26 having a through hole ahead of the vacuum application port 221 (on the tip side). Consequently, the outer casings 23 and 22 are supported coaxially, thus the negative pressure applied through the vacuum application port 221 is imparted to the space between the tip portions of the outer casings 23 and 22, thereby resulting in suction of the outer membrane 110 of the crystalline lens in the direction of the space G as shown in FIG. 4A.

While the cystotome hand piece for the trepanation of an outer membrane of the crystalline lens capsule having a function of sucking the outer membrane of the crystalline lens as shown in FIG. 4A is shown in FIG. 3, this type of a hand piece can also be applied to the hand piece having the function of sucking the outer membrane as shown in FIG. 2B. In the latter case, the outer casing 23 is not required and the opening 22a is provided on the outer casing 22 to apply a negative pressure into the outer casing 22 through the opening 22a as is shown in an enlarged portion $A_2$ of FIG. 3. Consequently, the negative pressure can be applied to the space between the outer casing 22 and the trepan bar 10. In addition, a large number of small holes may be provided around the trepan bar 10a at a position opposite to the opening 22a of the outer casing 22. Thus, the negative pressure can also be applied into the trepan bar 10.

The hand piece 210 described above or a hand piece subjected to proper modifications for improvement of this type can be employed for trepanation in order to adapt to various function of negative pressure application (for example, shown in FIGS. 2B and 4A to 4C), and the desirable trepanation can be performed.

(2) Removal of Crystalline Lens Substance

The second step of the lens replacement procedure of the present invention is to remove at least a portion of the lens substance through a small hole formed in the former step. The second step may be achieved by any appropriate technique, specifically, a tip of an open tube is inserted through the small hole to remove the lens substance, and then the lens substance is suctioned out of the capsule with a negative suction pressure applied to the other end of the tube. Of course, the outer diameter of the tube may be preferably smaller than that of the hole. The insertion tip should have such a configuration that does not damage the lens capsule.

It is preferable that the entire lens substance if possible be suctioned out of the capsule in order to achieve a higher degree of clearness after implantation. However, partial removal may be applied depending on the degree of cloudiness and/or conditions of the lens capsule and the lens substance.

Alternatively, another approach may be preferable depending on the condition of the lens, into which the lens capsule is inserted with a guide fiber in the lens removal step and an ultrasonic oscillating probe or a breaking laser is introduced into the lens to break the cloudy or completely opaque lens into small pieces, which are then aspirated from the capsule.

The closure may be used in this step of the present invention for removing the lens. An embodiment with the closure is described more in detail below.

(3) Direct Refilling of Lens Capsule with Injectable Compositions

The third step of the method according to the present invention uses a hydrophilic polymer that is an essential component of the injectable composition to be refilled directly into the lens capsule in place of the natural lens. The hydrophilic polymer used may be any hydrophilic material that dissolves, disperses or swells in water. They may be homopolymers; copolymers of a hydrophilic monomer and one or more hydrophobic monomer(s) to control water-solubility or viscosity; and modified polymers such as those obtained by reacting these homopolymer(s) and/or copolymer(s) with, for example, an isocyanate compound, an epoxy compound, or an end-capping agent, and those obtained by graft polymerization of the above-mentioned homopolymer(s) and/or copolymer(s). In addition, the hydrophilic polymer used may be a combination of two or more of the homopolymers, copolymers or modified polymers as long as they are compatible with each other. The hydrophilic polymer may be cross-linked to the extent that a desirable viscosity can be achieved.

Examplary hydrophilic polymers may include polysaccharides such as methylcellulose, hydroxypropyl cellulose, hydroxypropyl methylcellulose, chitin, and alginic acid; and synthetic polymers such as poly(meth)acrylic polymers, polyvinyl alcohol (PVA) polymers, polyvinyl pyrrolidone (PVP) polymers, and polyethylene glycol (PEG) polymers.

Examplary poly(meth)acrylic polymer may include poly (meth)acrylic acid, sodium poly(meth)acrylate, poly(meth) acrylamide, poly{N,N-dimethyl(meth)acrylamide}, poly{N-methyl(meth)acrylamide}, poly{N-ethyl(meth) acrylamide}, poly{N-propyl(meth)acrylamide}, poly{N- isopropyl(meth)acrylamide}, poly{N-butyl(meth)acrylamide}, poly(N-acryloylmorpholine), poly{2-hydroxyethyl(meth)acrylate}, poly {3-hydroxypropyl(meth)acrylate}, and poly{4-hydroxybutyl(meth)acrylate}.

Polyvinyl alcohol polymer may include for example, saponification products of a homopolymer of a vinyl ester such as vinyl acetate, vinyl butyrate, vinyl pivalate, and vinyl versatate, or a copolymer thereof; and saponification products of a copolymer of the above-mentioned vinyl esters and other copolymerizable monomer(s). Examplary copolymerizable monomer may include olefins such as ethylene, propylene, and 1-hexane; unsaturated carboxylic acids such as (meth)acrylic acid, crotonic acid, maleic acid, itaconic acid, and maleic anhydride, and salts or esters thereof, acrylamide such as (meth)acrylamide, N-alkyl (meth)acrylamide, N,N-dialkyl (meth)acrylamide, 2-(meth)acrylamide propanesulfonic acid and salts thereof, (meth)acrylamide propyldimethylamine and salts thereof; styrene; vinyl ethers such as methyl vinyl ether and t-butyl vinyl ether; N-vinyl amides such as N-vinyl pyrrolidone, N-vinyl formamide, and N-vinyl acetoamide; allyl compounds such as allyl acetate, allyl chloride, ally alcohol, allyl sulfonic acid and salts thereof, 8-hydroxy-1-octene; vinyl cyanides such as (meth)acrylonitrile; vinyl halides such as vinyl chloride, vinylidene chloride, vinyl fluoride, and vinylidene fluoride; and silane compounds such as vinyltrimethoxysilane. It is preferable that the copolymerizable monomer be copolymerized in an amount equal to or less than 20 mol %.

In the present invention, the above-mentioned polyvinyl alcohol polymer may be polymers obtained by reacting isocyanate compounds such as methyl isocyanate, ethyl isocyanate, isopropyl isocyanate, isobutyl isocyanate, phenyl isocyanate, tolyl isocyanate, and naphtyl isocyanate, or reacting epoxy compounds such as epoxypropane, epoxybutane, epoxycyclohexane, and epoxyethylbenzene, as well as polymers obtained by graft polymerization of the above-mentioned polyvinyl alcohol polymer with cerium ions.

Examples of the polyvinyl pyrrolidone polymer may include homopolymers of vinyl pyrrolidone, such as N-vinyl-2-pyrrolidone, N-vinyl-3-pyrrolidone, and N-vinyl-4-pyrrolidone, or copolymers thereof, and copolymers of the above-mentioned vinyl pyrrolidone and other copolymerizable monomer(s). The copolymerizable monomer may be same as those described in conjunction with the vinyl esters and the copolymerizable monomers for the polyvinyl alcohol polymers. It is preferable that the copolymerizable monomer be copolymerized in an amount equal to or less than 20 mol %.

Polyethylene glycol polymer may include for example, homopolymers of ethylene oxide (polyethylene glycol) and copolymers of ethylene oxide with a copolymerizable monomer such as epoxypropane, epoxybutane, epoxycyclohexane, or epoxyethylbenzene. It is preferable that the copolymerizable monomer be copolymerized in an amount equal to or less than 20 mol %.

In the present invention, the polymer obtained by reacting the above-mentioned polyethylene glycol polymer with an end-capping agent may be used. Examplary end-capping agent may include carboxylic acids acetic acid, butyric acid, valeric acid, hexanoic acid, octanoic acid, decanoic acid, and benzoic acid; and alcohols such as methanol, ethanol, isopropanol, butanol, hexanol, octanol, decanol, and phenol.

In the present invention, it is preferable that the polymer used be compatible in vivo with organisms for a long period of time without being metabolized, and have such a viscosity that it can flow through a fine needle, even when an injectable composition to be refilled directly into the lens capsule is prepared comprising a high content of the hydrophilic polymer. The hydrophilic polymers injectable with a fine needle are preferable for their potential of allowing a smaller hole in the lens capsule. Suitable hydrophilic polymers may include at least one polymer selected from the group consisting of polyvinyl alcohol polymers, polyvinyl pyrrolidone polymers, and polyethylene glycol polymers and, inter alia, a blend of a polyvinyl alcohol polymer and a polyvinyl pyrrolidone polymer.

The polyvinyl alcohol polymer may be preferably a saponification product of a homopolymer of a vinyl ester such as vinyl acetate, vinyl butyrate, vinyl pivalate, and vinyl versatate, or a copolymer thereof and, more preferably, a saponification product of a homopolymer of vinyl acetate. The polyvinyl pyrrolidone polymer may be preferably a homopolymer of N-vinyl-2-pyrrolidone. The polyethylene glycol polymer may be preferably a homopolymer of ethylene oxide (polyethylene glycol).

The viscosity of hydrophilic polymers may be preferably 50,000 cP or lower, more preferably, 30,000 cP or lower, and yet more preferably, 10,000 cP or lower.

The viscosity average polymerization degree of polyvinyl alcohol polymers may be preferably 30 or higher, more preferably 50 or higher, and most preferably 70 or higher, taking into account of the possible suppression of absorption in vivo of the polymer into the body of the organisms. For the injectable compositions comprising such polymers at a higher content, the viscosity should be as low as possible. Thus, the viscosity average polymerization degree thereof may be preferably 10,000 or lower, more preferably, 5,000 or lower, and most preferably, 2,000 or lower in terms of a desirable viscosity achieved. In addition, since it is required to maintain clarity for a long time with an environmental temperature at or a approximate body temperature, the saponification degree of polyvinyl alcohol polymers may be preferably 50 mol % or higher, more preferably 55 mol % or higher, and yet more preferably, 60 mol % or higher, taking into account of possible prevention of phase separation that may cause reduction in clarity. The saponification degree is preferably not higher than 99.8 mol %, more preferably, not higher than 99.5 mol %, and most preferably not higher than 99.0 mol %, taking into account of possible inhibition of clouding that may result from increase in degree of crystallization.

The number average molecular weight of polyvinyl pyrrolidone polymers may be preferably 3,000 or greater, more preferably, 4,000 or greater, and most preferably 5,000 or greater, taking into account of possible suppression of absorption in vivo of the polymer into the body of the organisms. For the injectable compositions comprising such polymers at a higher content, the viscosity should be as low as possible, thus the number average molecular weight thereof is preferably not greater than 3,000,000, more preferably, not greater than 2,000,000, and most preferably, not greater than 1,000,000, in terms of a desirable viscosity achieved.

The number average molecular weight of polyethylene glycol polymers may be preferably 200 or greater, and more preferably, 400 or greater, taking into account of possible suppression of absorption in vivo of the polymer into the body of the organisms. For the injectable compositions comprising such polymers at a higher content, the viscosity should be as low as possible, thus the number average molecular weight thereof may be preferably not greater than 1,000,000, more preferably, not greater than 800,000, and most preferably, not greater than 500,000, in terms of a desirable viscosity achieved.

A blend of a polyvinyl alcohol polymer and a polyvinyl pyrrolidone polymer is suitable because it allows complemental improvement of the time-dependent change in viscosity of the polyvinyl alcohol polymer and of the reduction in clarity of the polyvinyl pyrrolidone polymer, when the composition is prepared as a high-content solution. The blending ratio (by weight) of, for example, polyvinyl alcohol polymer/polyvinyl pyrrolidone polymer may be preferably in the range of 1/99 to 99/1, more preferably, 3/97 to 97/3, and most preferably 5/95 to 95/5, taking into account of a possible effect resulting from the blend.

The index of refraction of the injectable composition to be refilled directly into the lens capsule which is used in the present invention may be preferably 1.340 or higher, more preferably 1.345 or higher, and most preferably, 1.350 or higher, in order to provide desirable accommodation of the lens resulting from the relaxation and contraction of the ciliary muscle. It is much more desirable if a gradient refraction index (GRIN) lens of predetermined properties can be injected into the lens capsule.

The injectable composition to be refilled directly into the lens capsule for use in the present invention may advantageously comprise a high content of hydrophilic polymer, with having a low viscosity, taking into account of a possibility to allow a smaller hole penetrating through the lens capsule. The viscosity of the injectable composition to be refilled directly into the lens capsule may be preferably 50,000 cP or lower, more preferably, 30,000 cP or lower, and most preferably, 10,000 cP or lower, in order for surgeons to use a needle of a smaller diameter. When the lens capsule is refilled with an injectable composition with the above-mentioned viscosity range, the resultant lens implant has the accommodative ability to change its shape resulting from the relaxation and contraction of the ciliary muscle. Accordingly, the injectable composition according to the present invention is a suitable composition that can impart accommodative ability to the lens implant.

The visible light transmittance of the injectable composition to be refilled directly into the lens capsule which is used in the present invention may be preferably 50% or higher, more preferably, 55% or higher, and most preferably, 60% or higher in terms of achieved clarity. The visible light transmittance may be preferably 50% or higher taking into account of ensuring sufficient visual performance.

The content of the hydrophilic polymer in the injectable composition to be refilled directly into the lens capsule for use in the present invention is not limited specifically as long as desirable properties can be obtained. For example, the content may be preferably at least 1% by weight, more preferably, at least 3% by weight, and most preferably, 5% by weight, relative to the total weight of the injectable composition in terms of a desirable refraction of the resultant lens implant after the replacement. The content is preferably 90% by weight or less, more preferably, 85% by weight or less, and most preferably, 80% by weight or less, relative to the total weight of the injectable composition, in terms of facility of injection and inhibition of time-dependent change in viscosity as well as in clarity.

The injectable composition to be refilled directly into the lens capsule for use in the present invention may be preferably in the form of an aqueous solution or a gel of the above-mentioned hydrophilic polymer. A solvent used for dissolving or swelling the hydrophilic polymer into a solution or a gel may be, but not limited to, water, saline, intraocular irrigating solutions, and eye cleaning solutions.

The injectable composition to be refilled directly into the lens capsule for use advantageously in the present invention may contain, if desired, additives other than the hydrophilic polymer(s) as long as the properties of the composition are not deteriorated. Examples of such additives include colorants such as dyes, ultraviolet absorbers, antioxidants, stabilizers, surfactants, sequestration agents, defoamers, nutrition such as glucose, inorganic compounds such as sodium chloride, potassium chloride, calcium chloride, magnesium sulfate, sodium bicarbonate, sodium hydrogen phosphate, and boric acid, and eye cleansing/soothing agents such as oxidized glutathione. The substances listed above may be formulated in the injectable composition to be refilled directly into the lens capsule by using, for example, a formulation containing them. The formulation in this case may be based on, for example, saline, intraocular irrigating solutions, and eye cleaning solutions. Among these formulations, the saline and the intraocular irrigating solutions are preferable because they usually have an effect of equilibrating isotonicity in vivo. The intraocular irrigating solutions are more preferable that are similar in constitution to aqueous humor, have an effect of equilibrating isotonicity in vivo, and are used in cataract surgeries, glaucoma surgeries and other ophthalmic surgeries including vitreous surgeries to flush away eye irritants cleanse and sooth irritated eyes.

The injectable composition to be refilled directly into the lens capsule may be prepared by any appropriate technique such as by dissolving the hydrophilic polymer into water along with, if desired, an additive(s), dissolving a desirable additive(s) into an aqueous solution of the hydrophilic polymer, dissolving the hydrophilic polymer into an aqueous solution of a desirable additive(s), or dissolving the hydrophilic polymer into preparation having a desirable effect(s). It is preferable that the preparation be carried out under the condition that does not cause denaturation of the hydrophilic polymer and the additive(s). In Addition, the injectable composition to be refilled directly into the lens capsule may be prepared in a sterile manner or be injected into the lens capsule after a specified sterilization process. Considering that the composition should not be denatured after preparation and that it should be prepared in a sterile manner or be sterilized immediately before use, it is preferable that the injectable composition to be refilled directly into the lens capsule be provided in a vial. It is more preferable that the composition be provided in a cartridge for injection.

The term "direct(ly)" used herein in conjunction with the injectable composition to be refilled directly into the lens capsule means that the injectable composition is directly injected into the lens capsule rather than into a balloon placed in the lens capsule.

The injectable composition may be refilled into the lens capsule through a small hole by using a similar open tube to the one used to remove the lens substance. Alternatively, the injectable composition may be refilled by using a syringe. A needle of a smaller diameter is preferable to provide a smaller hole penetrating through the lens capsule. For example, the needle size may be preferably 16 gauge or smaller, more preferably, 18 gauge or smaller, and most preferably 20 gauge or smaller. Since the injectable composition to be refilled directly into the lens capsule has a low viscosity as described above, the composition can be readily refilled with such a fine needle.

(4) Closing the Hole of Crystalline Lens Capsule

After refilling the injectable composition to be refilled directly into the lens capsule, the small hole in the lens capsule is closed. The small hole may be closed by any closures such as a biocompatible patch, plug, or surgical adhesive, as long as the injected composition is not leaked for a long period of time.

Preferably, the hole closure is made of a gel or a soft plastic material which is highly stable and flexible, is not susceptible to chemical modification and decomposition, is non-toxic and compatible to tissues of organisms, and has physical and mechanical properties that may not cause damage to circumferential tissues. Examples of such materials may include hydrated gels such as polyvinyl alcohol (PVA) and polyhydroxyethyl methacrylate; and soft plastics such as silicon rubber and soft acrylic resins. When PVA gel is used, it is preferable that the gel be cross-linked to increase strength and rigidity. Cross-linking may be performed by, for example, freezing process or light irradiation process.

The hole closure may be manufactured by casting the gel or the soft plastic in, for example, a mold, followed by solidification therein. Preferably, the hole closure is a rod-shaped member having an enlarged portion provided at the tip of the rod-shaped member, a marginal protruding piece provided at a middle part of the rod-shaped member and the closed tubular section provided along the axial center of the rod-shaped member. For casting the closure, the rod-shaped member may be formed as a solid cylinder, cylindroid, or rectangular column. When a rectangular column-shaped rod-shaped member is used, it is preferable that the edges be chamfered to provide round corners.

The enlarged portion of the rod-shaped member may be formed integrally with the rod-shaped member at the end thereof. The shape of the enlarged portion may be conical, pyramidal, or hemispherical. Alternatively, a protrusion may be provided on a periphery of the rear edge of the cone, pyramid, or hemisphere.

The marginal protruding piece provided at a middle part of the rod-shaped member is a projection on the outer periphery thereof. It may be formed integrally with the rod-shaped member at the end thereof. Alternatively, the marginal protruding piece may be a ring member that is removable from the rod-shaped member. The ring member used may be a molded piece made of the above-mentioned gel or soft plastic, as well as metal, hard rubber, or hard plastic. It is preferable that the inner diameter of the ring member be smaller than the outer diameter of the rod-shaped member. When the marginal protruding piece is formed integrally as a single piece with the rod-shaped member, the piece should be formed such that the rear (trailing) edge of the enlarged portion at the tip of the rod-shaped member is spaced away from the anterior (leading) edge of the piece in a distance approximately equal to the thickness of a capsule shell of a crystalline lens.

The closed tubular section provided along the axial center of the rod-shaped member serves as a guide or a holder for insertion of a rigid tubular member such as a needle into the eye, which is molded such that it is closed when not being used. The closed tubular section may penetrate through the length from the tip of the enlarged portion to the tail end of the rod-shaped member, alternatively, the closed tubular section may be formed such that it extends from inside the enlarged portion to the tail end of the rod-shaped member. For the latter case, a rigid tubular can pass through the length from the anterior edge of the closed tubular section to the tip of the enlarged portion.

Figure 5:
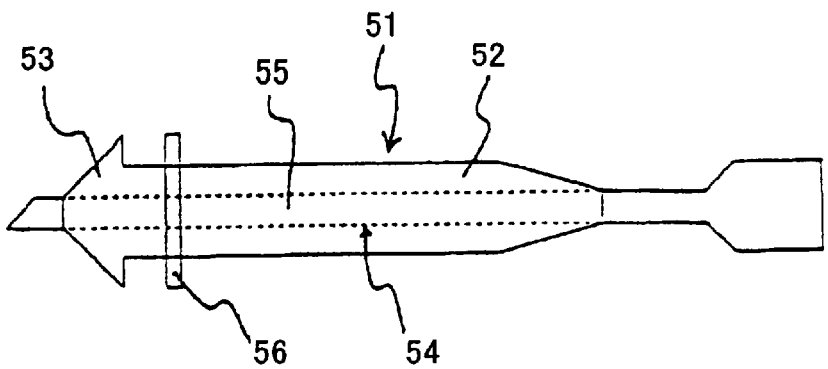
FIG. 5 is a side view showing an example of a hole closure according to one embodiment of the present invention.
Figure 6:
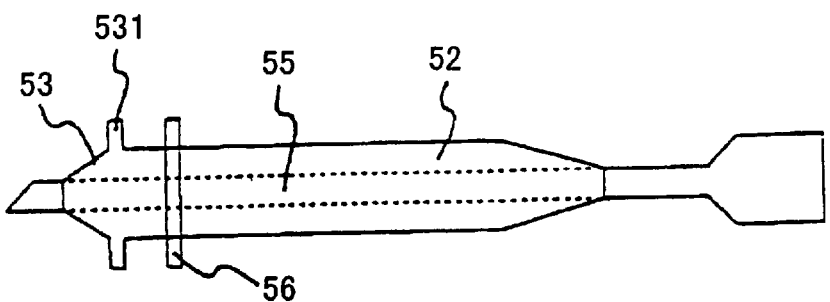
FIG. 6 is a side view showing an example of the hole closure according to another embodiment of the present invention.

FIG. 5 is a side view showing an example of a hole closure which is used advantageously in the method according to the present invention. A hole closure 51 has a rod-shaped member 52 of a substantially cylindrical shape. A conical enlarged portion 53 is provided at the tip end of the rod-shaped member 52. Along the axial center of the rod-shaped member 52, a closed tubular section 54 is provided in which a needle 55 is placed. A separate ring member 56 is movably fitted to the rod-shaped member 52 as the marginal protruding piece. FIG. 6 is a side view showing another examplary hole closure. The hole closure in FIG. 6 is similar to the one in FIG. 5 except for a projection 531 provided on the outer periphery of the enlarged portion 53.

Figure 7:
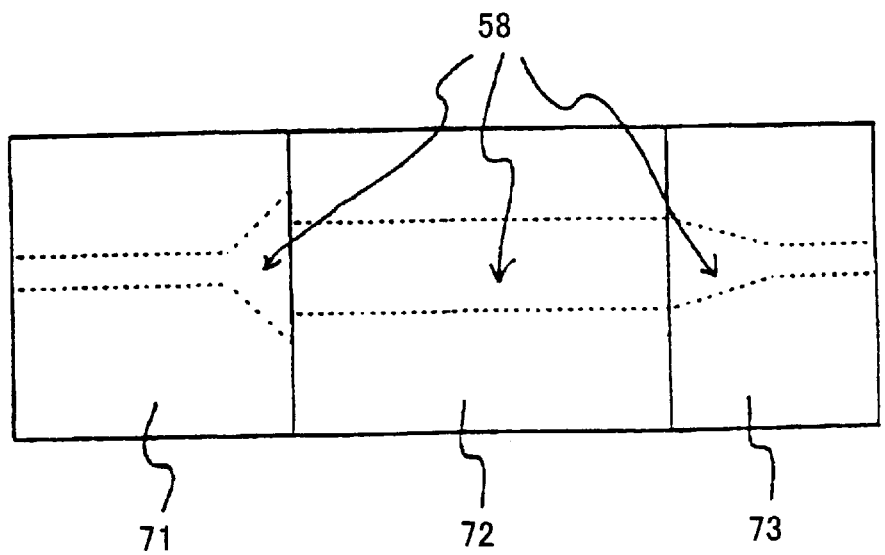
FIG. 7 is a plan view illustrating a mold for casting a hole closure shown in FIG. 4, and FIGS. 8(A), 8(B), 8(C) and 8(D) are views showing a method of crystalline lens replacement by using the hole closure according to the present invention.

The hole closure 51 illustrated in FIG. 5 may be formed by using a three-piece mold with mold sections 71, 72, and 73 as shown in FIG. 7. A gel or a soft plastic material is filled into a hollow space 58 within the mold and solidified therein. A straight core material may be placed along the axial center of the hollow space 58 before injection of the gel or the soft plastic material to form the closed tubular section 54 that serves as a guide for inserting and removing the needle 55 into and out of the hole closure. The diameter of the core used is equal to or smaller than that of the needle 55.

For example, When the hole closure shown in FIG. 5 is used for the crystalline lens, the outer diameter of the rod-shaped member 52 may be from 0.5 mm to 2.0 mm, preferably from about 0.8 mm to about 1.2 mm, the maximum diameter of the enlarged portion 53 is from 1.3 mm to 3.0 mm, preferably from about 1.2 mm to 2.0 mm, and the length between the tip of the enlarged portion 53 and the rear end of the rod-shaped member 52 is from 5.0 mm to 15.0 mm, preferably from about 6.0 mm to about 8.0 mm. The needle 55 for use in the present invention may have a size of about 20 gauge to 32 gauge.

The fourth step of closing the small hole in the lens capsule using the above-mentioned hole closure is described below.

First, the rigid tubular member such as the needle is inserted into the closed tubular section of the closure as described above thereby imparting rigidity to the closure made of a soft material. The enlarged portion of the closure at the tip thereof is then inserted into the capsular bag through the small hole in the lens capsule. A portion of the lens capsule shell surrounding the hole is pinched with the rear edge surface of the enlarged portion and the anterior edge surface of the marginal protruding piece. When the ring member is used as the marginal protruding piece, the ring member is previously fitted to the rod-shaped member in a backward position away from the tip and is then slid toward the tip. The rigid tubular member is then removed to close the small hole. A needless (unused) portion of the rod-shaped member may be finally cut out.

The rigid tubular member may be a solid core material rather than an open tubular needle when it is used only for the purpose of closing the small hole. However, the open tubular member such as a needle allows the closure to be used as a guide, thus removal of the lens substance and/or refilling of the lens capsule with the injectable composition to be refilled directly into the lens capsule can be accomplished through the rigid tubular member. In addition, swelling of the gel material or deformation of the soft plastic material used for the rod-shaped member allows the closed tubular section to remain closed even after the injectable composition is refilled into the lens capsule and the rigid tubular member is removed from the lens, which is preferable in terms of preventing leakage of the lens implant for a long period of time.

The crystalline lens replacement according to an embodiment of the present invention is described in conjunction with cataract surgery with a foldable artificial lens shown in FIG. 8.

A) A small hole 111 is formed penetrating through the outer membrane 110 that is the shell tissue of the lens 109, by irradiating a laser beam or by using a cystotome hand piece, according to the procedure described above. A guide fiber is inserted through the small hole 111 to introduce an ultrasonic oscillating probe or a breaking laser into the lens 109. The cloudy lens substance is then fragmented into small pieces and emulsified. At least a part of the emulsified pieces are aspirated through a suction tube 512.

B) An almost complete "capsule" of the lens is kept intact other than the small hole 111, with the ciliary body and cell tissues also remaining normal.

C) Then, the needle 55 is inserted into the hole closure 51 and the enlarged portion 53 thereof is inserted through the small hole 111. An injectable composition to be refilled directly into the lens capsule 113, which is a material of the lens implant, is then injected through the needle 55.

D) The lens 109 is refilled with the injectable composition to be refilled directly into the lens capsule 113 to restore its shape, thereafter the needle 55 is removed while the ring member 56 pushing against the outer membrane 110 of the lens capsule. The needless portion of the rod-shaped member 52 is finally cut out.

Since the needle 55 can be applied again into the closure 51 depending on the postoperative progress to further administer medicaments or drugs or inject transparent viscoelastic substances, it is possible to treat the patient promptly without invasion if time-dependent leakage of the lens implant occurs.

While the above-mentioned method of crystalline lens replacement according to the present invention may be performed advantageously to therapeutically treat cataracts, the present invention is not limited thereto and may be applied to other diseases associated with lens capsule disorders, such as lenticular astigmatism.

The lens replacement according to the present invention may be performed either in vivo or in vitro. However, it is particularly useful to apply this method to surgical operations in vivo because quick treatment with less invasion.

While the method of the present invention may be applied to various animals including human, it is advantageous that the method is applied to mammalian animals including domestic and farm animals such as, but not limited to, monkeys, dogs, rabbits, cats, hamsters, horses, and cattle.

EXAMPLES

The present invention is described specifically and in more detail below with reference to examples thereof. However, these examples should not be construed as any limitation of the present invention.

1. Closure Manufacturing

[Manufacturing Example 1]

Twenty g of fully saponified PVA with polymerization degree of 2,000 was molten in 100 g of a mixed solvent (80:20 weight ratio) of dimethyl sufoxide (DMSO) and purified water. The resultant highly viscous solution was filled into a resin mold shown in FIG. 6, which was then subjected to three freeze-thaw cycles each consisting of freezing in a freezer at −20° C. for 3 hours and thawing to the atmospheric temperature. The hole closure was removed from the mold and left for several days in a 50% aqueous solution of ethanol while stirring. The hole closure was then placed in saline and left for additional several days while stirring to produce a closure of the PVA hydrated gel (1.0 mm in diameter, 10.0 mm in length of the rod-shaped member) substituted by saline.

[Manufacturing Example 2]

A ring member (0.2 mm in thickness, 2.0 mm in outer diameter, and 1.0 mm in inner diameter) was formed using the PVA gel similar to the one used in Manufacturing Example 1. The ring member was then fitted to the hole closure formed in Manufacturing Example 1.

[Manufacturing Example 3]

Five g of NCL (silicon substrate, Shin-Etsu Chemical Co., Ltd.) and 0.5 g of C-NCL (catalyst, Shin-Etsu Chemical Co., Ltd.) were stirred in a glass vessel. The mixture was subjected to defoaming and filled into the mold shown in FIG. 6. The mold was placed into a press at a pressure of 1.5 kgf/cm$^2$ and heated on a hot plate at 100° C. for 30 minutes. The piece was then removed from the mold and subjected to plasma processing to produce a colorless and transparent hole closure made of silicon rubber, having the same dimensions as the one obtained in Manufacturing Example 1.

[Manufacturing Example 4]

Five g of X-32-159-6 (silicon substrate, Shin-Etsu Chemical Co., Ltd.) and 0.5 g of CX-32-159-6 (silicon substrate, Shin-Etsu Chemical Co., Ltd.) were stirred in a glass vessel The mixture was subjected to defoaming and filled into the mold shown in FIG. 6. The mold was placed into a press at a pressure of 1.5 kg/cm$^2$ and heated on a hot plate at 100° C. for 30 minutes. The piece was then removed from the mold and subjected to plasma processing to produce a colorless and transparent hole closure made of silicon rubber, having the same dimensions as the one obtained in Manufacturing Example 1.

[Manufacturing Example 5]

The procedure in Manufacturing Example 1 was repeated to form a PVA gel closure except that the rod-shaped member was 2.0 mm in diameter. In addition, the procedure in Manufacturing Example 2 was also repeated to form a PVA gel ring member except that the inner diameter of the gel was 2.0 mm.

2. Examples of Lens Replacement

Viscosity, index of refraction, and visible light transmittance of the injectable compositions to be refilled directly into the lens capsule described in the following Examples and Comparative Examples were measured or assessed as follows.

[Viscosity of the Injectable Composition]

Viscosity was measured with an E-type cone-plate viscometer (Visconic-EHD, Tokimec Inc.) equipped with a thermostat, at 35° C., for the injectable composition and the lens implant extracted 6 months after the refilling into the lens capsule. Percent change in viscosity was calculated according to the following equation for the injectable composition before refilling into and after extracted from the lens capsule of a rabbit.

$$\text{Percent Change}(\%) = \frac{(\text{Viscosity Before Refilling}) - (\text{Viscosity After Extraction})}{(\text{Viscosity Before Refilling})} \times 100$$

[Index of Refraction of the Injectable Composition]

Index of refraction was measured with a refractometer (Abbe refractometer Type 1, Atago Co., Ltd.) equipped with a thermostat, at 35° C., for the injectable composition and the lens implant extracted 6 months after the refilling into the lens capsule. Percent change in index of refraction was calculated according to the following equation for the injectable composition before refilling into and after extracted from the lens capsule of a rabbit.

[Visible Light Transmittance of the Injectable Composition]

Visible light transmittance was measured for the injectable composition and the lens implant extracted 6 months after the refilling into the lens capsule. The injectable composition and the lens implant were left for a while in a thermostat at 35° C., and then the visible right transmittance was measured immediately with a haze meter (TC-H/CL available from Tokyo Denshoku Co., Ltd.) at a wavelength of 380–780 nm. Percent change in visible light transmittance was calculated according to the following equation for the injectable composition before refilling into and after extracted from the lens capsule of a rabbit.

$$\text{Percent Change (\%)} = ((\text{Visible Light Transmittance Before Refilling}) - (\text{Visible Light Transmittance After Extraction}))/(\text{Visible Light Transmittance Before Refilling}) \times 100$$

[Example 1]

Fifteen parts by weight of polyvinyl alcohol (PVA405; Kuraray Co., Ltd.; viscosity average polymerization degree: 500; saponification degree: 82 mol %) used as a hydrophilic polymer was dissolved in 85 parts by weight of saline (Otsuka Pharmaceutical Co., Ltd.) to prepare a liquid injectable composition to be refilled directly into the lens capsule. The injectable composition was 200 cP in viscosity, 1.358 in index of refraction, and 99% in visible light transmittance. This injectable composition was sealed into an injection cartridge, which was subjected to autoclave sterilization.

A small hole of about 1 mm in diameter was formed penetrating through the lens capsule of a rabbit with a cystotome hand piece shown in FIG. 3. Next, the lens substance was removed almost completely from the lens capsule through the hole by means of phacoemulsification. A 27-gauge needle was applied through the closure formed in accordance with Manufacturing Example 2. The tip of the closure was inserted through the hole followed by refilling of the above-mentioned injectable composition into the lens capsule through the needle. After refilling, the ring member was pushed ahead with a forceps to pinch the capsule with the enlarged portion, thereby fixing the closure. The needle was then removed and the needless portion of the rod-shaped member was cut out to close the hole.

Six months after the surgery, the lens of the rabbit was extracted and visually observed by naked eyes. Neither leakage of the injectable composition nor histological abnormalities, such as capsule wrinkles, capsular breakage, and inflammation in and adhesion of the lens capsule, were found. The physical properties of the lens implant were almost identical to those of the injectable composition before refilling. Viscosity, index of refraction, and visible light transmittance of the lens implant were measured in the manner described above and were assessed as percent change. The results along with the findings are given in the Table 1 below.

[Example 2]

Forty parts by weight of poly(N-vinyl-2-pyrrolidone) (K-15; Gokyo Trading Co., Ltd.; average molecular weight: 10,000) used as a hydrophilic polymer was dissolved in 60 parts by weight of Opeguard MA® (Senju Pharmaceutical Co., Ltd.) to prepare a liquid injectable composition to be refilled directly into the lens capsule. The injectable composition was 370 cP in viscosity, 1.410 in index of refraction, and 87% in visible light transmittance. This injectable composition was sealed into an injection cartridge, which was subjected to autoclave sterilization.

A small hole of about 1 mm in diameter was formed penetrating through the lens capsule of a rabbit with a light guide having therein an optical fiber bundle of 1 mm in diameter. The lens capsule had previously been stained with an aqueous solution of indocyanine green (Daiichi Pharmaceutical Co., Ltd.; Diagnogreen® Injection) that optimizes laser energy absorption at a certain wavelength. A semiconductor laser with an optical output of 2 W was used as a light source at a wavelength of 600–1200 nm to irradiate the stained lens capsule placed immediately adjacent to the tip of the light guide, with almost no space therebetween. Next, the lens substance was removed almost completely from the lens capsule through the hole by means of phacoemulsification. The above-mentioned injectable composition was refilled into the lens capsule through the hole using a 24-gauge needle until the lens capsule regains its original shape before surgery. Then, the hole closure described above in Manufacturing Example 4 was used to plug the hole.

Six months after the surgery, the lens of the rabbit was extracted and visually observed by naked eyes. Neither leakage of the injectable composition nor histological abnormalities, such as capsule wrinkles, capsular breakage, and inflammation in and fixation of the lens capsule, were found. The physical properties of the injectable composition were almost identical before and after refilling. Viscosity, index of refraction, and visible light transmittance thereof were measured in the manner described above and were assessed as percent change. The results along with the findings are given in the Table 1 below. It should be noted that Opeguard MA® is an intraocular irrigating solution having the following formulation: 1.5 mg of glucose, 6.6 mg of NaCl, 0.36 mg of KCl, 0.18 mg of $CaCl_2$, 0.3 mg of $MgSO_4$, and 2.1 mg of $NaHCO_3$, per 1 mL of the solution.

[Example 3]

Sixty parts by weight of polyethylene glycol (PEG 1000; Wako Co.; average molecular weight: 1,000) used as a hydrophilic polymer was dissolved in 40 parts by weight of purified watei (Otsuka Pharmaceutical Co., Ltd.) to prepare a liquid injectable composition to be refilled directly into the lens capsule. The injectable composition was 440 cP in viscosity, 1.442 in index of refraction, and 97% in visible light transmittance. This injectable composition was sealed into an injection cartridge, which was subjected to autoclave sterilization.

The procedure in Example 1 was repeated to form a small hole penetrating through the lens capsule of a rabbit. A 21-gauge needle was applied in the hole closure formed according to the procedure in Manufacturing Example 5. The tip of the closure was inserted into the hole. Most of the vitreous body of the rabbit was aspirated. Then, the above-mentioned injectable composition was refilled through the same needle until the lens capsule regains its original shape before surgery. The closure was fixed with the ring member, the needle was removed, and the needless portion of the rod-shaped member was cut out to plug the hole. The hole in the lens capsule was not larger than 1 mm. Six months after the surgery, the lens of the rabbit was extracted and visually observed by naked eyes. Neither leakage of the injectable composition nor histological abnormalities, such as capsule wrinkles, capsular breakage, and inflammation in and adhesion of the lens capsule, were found. The physical properties of the lens implant were almost identical to those of the injectable composition before refilling. Viscosity, index of refraction, and visible light transmittance thereof were measured in the manner described above and were assessed as percent change. The results along with the findings are given in the Table 1 below.

TABLE 1

|  | Example 1 | Example 2 | Example 3 |
| --- | --- | --- | --- |
| Polymer [bland] (parts by weight) | | | |
| PVA [405] | 15 | — | — |
| PVP [K-15] | — | 40 | — |
| PEG [#1000] | — | — | 60 |
| Solvent (parts by weight) | | | |
| Saline | 85 | — | — |
| Opeguard MA | — | 60 | — |
| Purified Water | — | — | 40 |
| Change in Physical Properties (Percent change) | | | |
| Viscosity | 10%> | 10%> | 10%> |
| Index of Refraction | 10%> | 10%> | 10%> |
| Visible Light Transmittance | 10%> | 10%> | 10%> |
| Findings Observed | | | |
| Diameter of Small Hole After 6 month Upon Extraction | 1 mm> Unchanged | 1 mm> Unchanged | 1 mm> Unchanged |

[Example 4]

Twenty parts by weight of polyvinyl alcohol (PVA205; Kuraray Co., Ltd.; viscosity average polymerization degree: 500; saponification degree: 88 mol %) and 20 parts by weight of poly(N-vinyl-2-pyrrolidone) (KT30; Gokyo Trading Co., Ltd.; average molecular weight: 10,000), both of which were used as a hydrophilic polymer were dissolved in 60 parts by weight of Opeguard MA® (Senju Pharmaceutical Co., Ltd.) to prepare an injectable composition for the lens capsule. The injectable composition was 700 cP in viscosity, 1.411 in index of refraction, and 93% in visible light transmittance. This injectable composition was sealed into an injection cartridge, which was subjected to autoclave sterilization.

The procedure in Example 2 was repeated except that the light guide used to form a small hole of about 1 mm in diameter had a condenser (50 mm focal length; a GRIN rod lens SELFOC; Nippon Sheet Glass Co., Ltd.) provided at the tip end thereof, along with the optical fiber bundle of 1 mm in diameter. The above-mentioned injectable composition was refilled into the lens capsule of a rabbit, from which the lens substance had been extracted almost completely, through the hole using a 24-gauge needle as in Example 2 until the lens capsule regains its original shape before surgery. The hole was then plugged. The diameter of the hole in the lens capsule was not larger than 1 mm. Six months after the surgery, the lens of the rabbit was extracted and visually observed by naked eyes. Neither leakage of the injectable composition nor histological abnormalities, such as capsule wrinkles, capsular breakage, and inflammation in and adhesion of the lens capsule, were found. The physical properties of the lens implant were almost identical to those of the injectable composition before refilling. Viscosity, index of refraction, and visible light transmittance thereof were measured in the manner described above and were assessed as percent change. The results along with the findings are given in the Table 2 below.

[Example 5]

Thirty-five parts by weight of sodium itaconate-polyvinyl alcohol copolymer (KL-504; Kuraray Co., Ltd.; viscosity average polymerization degree: 400; itaconic acid copolymerization degree: 1 mol %; saponification degree: 75 mol %) used as a hydrophilic polymer was dissolved in 65 parts by weight of saline (Otsuka Pharmaceutical Co., Ltd.) to prepare a injectable composition gel to be refilled directly into the lens capsule. The injectable composition was 8800 cP in viscosity, 1.403 in index of refraction, and 82% in visible light transmittance. This injectable composition was sealed into an injection cartridge, which was subjected to autoclave sterilization.

The procedure in Example 2 was repeated to refill the injectable composition into the lens capsule of a rabbit, from which the lens substance had been extracted almost completely, through the hole using a 22-gauge needle until the lens capsule regains its original shape before surgery. The hole was then plugged. The diameter of the hole in the lens capsule was not larger than 1 mm. Six months after the surgery, the lens of the rabbit was extracted and visually observed by naked eyes. Neither leakage of the injectable composition nor histological abnormalities, such as capsule wrinkles, capsular breakage, and inflammation in and adhesion of the lens capsule, were found. The physical properties of the lens implant were almost identical to those of the injectable composition before refilling. Viscosity, index of refraction, and visible light transmittance thereof were measured in the manner described above and were assessed as percent change. The results along with the findings are given in the Table 2 below.

TABLE 2

|  | Example 4 | Example 5 |
| --- | --- | --- |
| Polymer [bland] (parts by weight) | | |
| PVA [205] | 20 | — |
| PVP [KL-504] | — | 35 |
| PVP [K-30] | 20 | — |
| Solvent (parts by weight) | | |
| Saline | — | 65 |
| Opeguard MA | 60 | — |
| Change in Physical Properties (Percent Change) | | |
| Viscosity | 10%> | 10%> |
| Index of Refraction | 10%> | 10%> |
| Visible Light Transmittance | 10%> | 10%> |
| Findings Observed | | |
| Diameter of Small Hole After 6 month Upon Extraction | 1 mm> Unchanged | 1 mm> Unchanged |

[Comparative Example 1]

One hundred parts by weight of methacrylate ester (X-22-174DX; Shin-Etsu Chemical Co., Ltd.) containing polydimethyl siloxane (consisting of dimethyl siloxane repeat units of 60 in average) as a photopolymerizable monomer was mixed with 1 part by weight of acetophen (Wako Co.) as a photoinitiator to prepare an injectable material. This injectable material was then sealed into an injection cartridge.

The procedure in Example 1 was repeated to refill the injectable material into the lens capsule of a rabbit, from which the lens substance had been extracted almost completely, through the hole using a 22-gauge needle until the lens capsule regains its original shape before surgery. The hole was then plugged with the hole closure obtained in accordance with Manufacturing Example 4.

Subsequently, a halogen beam was irradiated to harden the above-mentioned monomer. The diameter of the hole in the lens capsule was not larger than 1 mm. Six months after the surgery, the lens of the rabbit was extracted and visually observed by naked eyes. The monomer was solidified and fluidity of the lens was lost. It was apparent that the lens formed in this Comparative Example could not accommodate by the relaxation and contraction of the ciliary muscle. In addition, inflammation was found on the epithelium of the lens. Non-polymerized polymer or the photoinitiator was expected to be responsible for the inflammation. In this Comparative Example, the injectable material before injection is a polymerizable monomer composition, which can be polymerized into a polymer after injection. Therefore, no measurement was made for viscosity, index of refraction, and visible light transmittance. Thus observed findings are given in the Table 3 below.

[Comparative Example]

A circular hole was formed in the anterior capsule of a rabbit by using circular capsulorhexis according to conventional procedures of cataract surgery. Most of the lens cortex was removed by phacoemulsification. Next, a silicone balloon equipped with a silicone tube was inserted into the lens capsule. HEALON (Pharmacia Inc.; 10 mg of sodium hyaluronate, 8.5 mg of NaCl, 0.28 mg of $Na_2HPO_4\text{-}2H_2O$, and 0.04 mg of $NaH_2PO_4\text{-}H_2O$, per 1 mL of the solution) was refilled from one side. There was no other choice to form a hole of 5 mm or larger in the sclera and lens capsule for insertion of the balloon into the eye. Six months after the surgery, the lens of the rabbit was extracted and visually observed by naked eyes. As a result, a space was found in the lens capsule. It was apparent that only insufficient visual performance was achieved. Viscosity, index of refraction, and visible light transmittance thereof were measured in the manner described above and were assessed as percent change. The results along with the findings are given in the Table 3 below.

TABLE 3

|  | Comparative Example 1 | Comparative Example 2 |
| --- | --- | --- |
| Polymer [bland] (parts by weight) | | |
| Silicon Monomer [X-22-174DX] | 100 | — |
| Acetophenone [-] | 1 | — |
| Sodium Hyaluronate [HEALON] | — | 1 |
| Solvent (parts by weight) | | |
| PBS | — | 99 |
| Change in Physical Properties (Percent change) | | |
| Viscosity | — | 10%> |
| Index of Refraction | — | 10%> |
| Visible Light Transmittance | — | 10%> |
| Findings Observed | | |
| Diameter of Small Hole | 1 mm> | 5 mm< |
| After 6 month Upon Extraction | Inflammation Found | Unadapted Shape |

As apparent from the results shown in Tables 1 and 2, the injectable compositions to be refilled directly into the lens capsule according to Examples 1–5 have a sufficiently low viscosity, which allows them to deform in cooperation with the change in shape of the lens capsule resulting from the relaxation and contraction of the ciliary muscle. Furthermore, the injectable compositions to be refilled directly into the lens capsule used all have a high refractive power, so that the lens implant formed after refilling has the accommodative ability inherent to the natural lens. In addition, no change in formulation and physical properties due to, for example, metabolism was found in vivo. The lens implant keeps its clarity as well as compatibility with bodies of organisms for a long period of time. Thus, it was suggested that the injectable composition is useful as a replacement for the crystalline lens substance, which is to be injected directly into the lens capsule. Moreover, the injectable composition to be refilled directly into the lens capsule according to the present invention may be injected through a fine, right-after injection needle. This facilitates injection operation and allows reduction in size of the bole to be formed in the lens capsule.

[Effect of the Invention]

As described above, the method of crystalline lens replacement according to the present invention is highly stable and safe, allows surgical operations in a relatively short period of time with extremely less invasion. The natural accommodation of the lens is restored after the surgery. Desirable clarity is maintained for a long period of time. Therefore, a good prognosis can be achieved for patients suffered from, for example, cataracts.

What is claimed is:

1. A method of crystalline lens replacement, comprising the steps of:
   (a) forming a small hole penetrating through a crystalline lens capsule;
   (b) removing at least a part of the crystalline lens substance through the hole;
   (c) refilling the crystalline lens capsule with an injectable liquid composition comprising a hydrophilic polymer, the injectable liquid composition to be injected directly into the lens capsule through the hole; and
   (d) closing the hole.

2. The method according to claim 1, wherein the hole is closed by using a hole closure comprising a rod-shaped member made of a gel or a soft plastic material having an enlarged portion at the tip of the rod-shaped member, a marginal protruding piece provided at a middle part of the rod-shaped member, and a closed tubular section provided along the axial center of the rod-shaped member.

3. The method according to claim 2, wherein the hole closure has the closed tubular section penetrating from a tip of the enlarged portion to a tail end of the rod-shaped member.

4. The method according to claim 2, wherein the closed tubular section extends from inside the enlarged portion to a tail end of the rod-shaped member, and is capable of passing through a length measured from an anterior edge of the closed tubular section to the tip of the enlarged portion.

5. The method according to claim 2, wherein the hole closure includes a rigid tubular member that is longitudinally slidable in the closed tubular section and is removable from the closed tubular section.

6. The method according to claim 2, wherein the closing step comprises the steps of:
   (a) inserting the rigid tubular member into the closed tubular section of the hole closure;
   (b) inserting the enlarged portion provided on the tip of the closure into the crystalline lens through the hole;
   (c) pinching a portion of the lens capsule surrounding the hole with a rear edge surface of the enlarged portion and an anterior edge surface of the marginal protruding piece; and
   (d) pulling out the rigid tubular member, thereby closing the hole with the remaining closure.

7. A method of crystalline lens replacement, comprising the steps of:
(a) forming a small hole penetrating through a crystalline lens capsule;
(b) inserting a rigid tubular member that is longitudinally slidable in and removable from a closed tubular section, into the closed tubular section of a hole closure comprising a rod-shaped member made of a gel or a soft plastic material having an enlarged portion at the tip of the rod-shaped member, a marginal protruding piece provided at a middle part of the rod-shaped member and the closed tubular section provided along the axial center of the rod-shaped member, thereafter inserting said enlarged portion through the hole into the crystalline lens;
(c) ejecting a head of the rigid tubular member from the tip of the enlarged portion, and removing the crystalline lens substance through the rigid tubular member;
(d) refilling the crystalline lens capsule with an injectable liquid composition comprising a hydrophilic polymer, the injectable liquid composition to be injected directly into the lens capsule through the rigid tubular member; and
(e) pinching a portion of the lens capsule surrounding the hole with a rear edge surface of the enlarged portion and an anterior edge surface of the marginal protruding piece, and pulling out the rigid tubular member thereby closing the hole with the remaining closure.

8. The method according to claim 7, wherein the marginal protruding piece is a separate removable ring member.

9. The method according to claim 2, wherein the gel comprises cross-linked polyvinyl alcohol.

10. The method according to claim 2, wherein the soft plastic is silicon rubber.

11. The method according to claim 1, wherein the injectable composition comprises 1% to 90% by weight of hydrophilic polymer.

12. The method according to claim 1, wherein the injectable composition to be injected directly into the lens capsule has a viscosity of 50,000 cP or lower.

13. The method according to claim 12, wherein the injectable composition to be injected directly into the lens capsule has an index of refraction of 1.340 or higher and a visible light transmittance of 50% or more.

14. The method according to claim 1, wherein the hydrophilic polymer is at least one polymer selected from the group consisting of polyvinyl alcohol polymers, polyvinyl pyrrolidone polymers and polyethylene glycol polymers.

15. The method according to claim 14, wherein the hydrophilic polymer comprises a polyvinyl alcohol polymer and a polyvinyl pyrrolidone polymer.

16. The method according to claim 1, wherein the method of crystalline lens replacement is performed on an animal including human.

17. The method according to claim 1, wherein the method of crystalline lens replacement is performed on a patient suffering from cataract, and the opacified crystalline lens substance is removed at the removing step.

18. The method according to claim 1, wherein the hole is formed by irradiation of laser beam at the forming step.

19. The method according to claim 18, wherein a light guide is used which comprises a condensing lens having a focal length of 1 to 500 mm provided on a tip of said light guide.

20. The method according to claim 1, wherein the hole is formed by using a cystotome hand piece at the forming step.

21. The method according to claim 20, wherein the cystotome hand piece comprises a rotary shaft, a first motor for rotating the rotary shaft, a second motor for longitudinally moving the first motor and the rotary shaft integrally, a trepan bar removably attached to a tip of the rotary shaft, a fixed outer casing through which the trepan bar is inserted, and means for applying a negative pressure to an interspace of an inside of the trepan bar or between the trepan bar and the fixed outer casing, and wherein the rotary shaft provided integrally with the first motor is moved forward through the second motor to eject a tip of the trepan bar from the outer casing during the hole forming operation, and the rotary shaft provided integrally with the first motor is usually moved backward through the second motor to store the tip of the trepan bar within the outer casing.

* * * * *

UNITED STATES PATENT AND TRADEMARK OFFICE
CERTIFICATE OF CORRECTION

PATENT NO. : 6,413,262 B2
DATED : July 2, 2002
INVENTOR(S) : Saishin Mototsugu

It is certified that error appears in the above-identified patent and that said Letters Patent is hereby corrected as shown below:

<u>Title page,</u>
In the name of the first listed inventor: please replace "Motosugu" with
-- Mototsugu --

Signed and Sealed this

Nineteenth Day of November, 2002

Attest:

Attesting Officer

JAMES E. ROGAN
*Director of the United States Patent and Trademark Office*

UNITED STATES PATENT AND TRADEMARK OFFICE
CERTIFICATE OF CORRECTION

PATENT NO.   : 6,413,262 B2
DATED        : July 2, 2002
INVENTOR(S)  : Saishin et al.

It is certified that error appears in the above-identified patent and that said Letters Patent is hereby corrected as shown below:

<u>Title page,</u>
In the name of the first listed inventor: please replace "Motosugu" with
-- Mototsugu --

This certificate supersedes Certificate of Correction issued November 19, 2002

Signed and Sealed this

Eleventh Day of February, 2003

JAMES E. ROGAN
*Director of the United States Patent and Trademark Office*